United States Patent [19]

Waldner et al.

[11] Patent Number: 4,999,426
[45] Date of Patent: Mar. 12, 1991

[54] PREPARATION OF 4-AZASACCHARINES

[75] Inventors: Adrian Waldner, Allschwil; Willy Meyer, Riehen, both of Switzerland

[73] Assignee: Ciba-Geigy Corporation, Ardsley, N.Y.

[21] Appl. No.: 385,851

[22] Filed: Jul. 26, 1989

Related U.S. Application Data

[62] Division of Ser. No. 242,834, Sep. 12, 1988, Pat. No. 4,889,933.

[30] Foreign Application Priority Data

Sep. 18, 1987 [CH] Switzerland .......................... 3620/87

[51] Int. Cl.$^5$ ........................................... C07D 513/04
[52] U.S. Cl. ..................................... 544/127; 546/114
[58] Field of Search ........................ 546/114; 544/127

[56]  References Cited

U.S. PATENT DOCUMENTS 4,754,033  6/1988  Waldner ................................ 546/92

FOREIGN PATENT DOCUMENTS 2113927  6/1972  France .
1368948  10/1974  United Kingdom .

OTHER PUBLICATIONS

Weiler et al., J. Het. Chem., 15, pp. 1299–1302 (1978).

Primary Examiner—Mary C. Lee
Assistant Examiner—Bernard I. Dentz
Attorney, Agent, or Firm—Kevin T. Mansfield; Edward McC. Roberts

[57]  ABSTRACT

Compounds of formula I

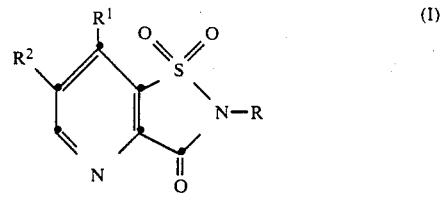

in which R is H, or an aliphatic or aromatic radical, $R^1$ is alkyl, $R^2$ is alkyl, alkoxy, aryl, aryloxy, aralkyl, alkaryl, aralkyloxy, alkaryloxy, alkaralkyl or alkaralkyloxy, and one of $R^1$ and $R^2$ is H and the other has the meaning given above. These compounds are intermediates for the preparation of herbicidal sulfonylureas.

2 Claims, No Drawings

PREPARATION OF 4-AZASACCHARINES

This is a divisional of application Ser. No. 242,834 filed on Sept. 12, 1988 now U.S. Pat. No. 4,889,933.

The invention relates to mono- or di-substituted 4-aza-saccharines, to mono- or di-substituted 4-aza-dihydro- or -tetrahydro-saccharines as intermediates and to processes for the preparation thereof.

R. F. Sauers et al. describe herbicides based on sulfonylureas in ACS Symposium Series 255, pages 21–28, (1984). Herbicidally active pyridylsulfonyl ureas are described, for example, in EP-A-0 013 480, EP-A-0 084 224, EP-A-0 097 122, EP-A-0 126 711 and EP-A-0 139 612. The multi-stage processes for the preparation thereof are uneconomical and the starting materials are difficult to obtain.

EP-A-0 172 140 describes the preparation of pyridine-2,3-dicarboxylic acids by the Diels-Alder reaction of 1-azadienes with ethylene-1,2-dicarboxylic acid derivatives to form 1-aminotetrahydropyridine-2,3-dicarboxylic acid derivatives, removal of the amino group and subsequent oxidation of the resulting 1,4-dihydropyridines.

The invention relates to compounds of formula I

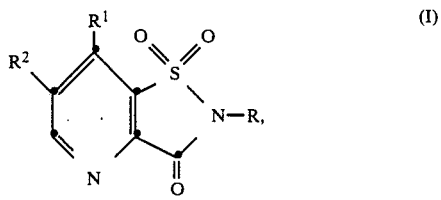

in which
R is H, linear or branched $C_1$–$C_{20}$alkyl, $C_2$–$C_{20}$alkenyl or $C_2$–$C_{20}$alkynyl, $C_3$–$C_{10}$cycloalkyl, $C_4$–$C_{20}$cycloalkylalkyl, $C_4$–$C_{20}$alkylcycloalkyl, $C_5$–$C_{20}$alkylcycloalkylalkyl, $C_6$–$C_{14}$aryl, $C_7$–$C_{20}$-aralkyl or -alkaryl or $C_8$–$C_{20}$alkaralkyl, each of which is unsubstituted or substituted by —OH, —CN, halogen, $C_1$–$C_{12}$-alkoxy or -alkylthio, $C_6$–$C_{10}$aryl-oxy or -thio, $C_7$–$C_{16}$-aralkyloxy, -alkaryloxy, -aralkylthio or -alkarylthio, $C_8$–$C_{18}$alkaralkyloxy or -thio, —NR³R⁴, —COOR⁵, —OCOR⁶, —CONR³R⁴ or by —NR³COR⁶, in which each of R³ and R⁴, independently of the other, is $C_1$–$C_{12}$alkyl, $C_5$- or $C_6$-cycloalkyl, $C_6$–$C_{10}$aryl, $C_7$–$C_{16}$aralkyl or $C_8$–$C_{16}$alkaralkyl or R³ and R⁴ together are tetra- or penta-methylene or 3-oxapentylene, R⁵ is H, $C_1$–$C_{12}$alkyl, phenyl, benzyl, cyclohexyl or cyclopentyl and R⁶ is $C_1$–$C_{12}$acyl,
R¹ is H, or linear or branched $C_1$–$C_{12}$alkyl which is unsubstituted or substituted by hydroxy, halogen, cyano, $C_1$–$C_4$alkoxy, carboxy, $C_1$–$C_{12}$acyloxy or by $C_1$–$C_4$alkoxycarbonyl, R² is H, or $C_1$–$C_{12}$-alkyl or -alkoxy, $C_6$–$C_{10}$-aryl or -aryloxy, $C_7$–$C_{16}$-aralkyl, -alkaryl, -alkaryloxy or -aralkyloxy, or $C_8$–$C_{16}$alkaralkyloxy, which are unsubstituted or substituted by hydroxy, halogen, cyano, $C_1$–$C_4$alkoxy, carboxy, $C_1$–$C_{12}$acyloxy or by $C_1$–$C_4$alkoxycarbonyl.

R as alkyl contains preferably from 1 to 12, especially from 1 to 8, carbon atoms. In a preferred sub-group, R is α,α-branched alkyl having especially from 4 to 12 carbon atoms. Examples of alkyl are methyl, ethyl, n- and iso-propyl, n-, iso- and tert.-butyl, 1,1-dimethylprop-1-yl, pent-1-, -2- or -3-yl, 1,1-, 1,2-, 1,3- or 2,2-dimethylprop-1-yl, 1,2,2-trimethylprop-1-yl, 1-, 2- or 3-hexyl, 1,1-, 1,2-, 1,3-, 1,4-, 2,3- or 3,4-dimethylbut-1-yl, 1,1,2,2-tetramethylethyl, 1-, 2-, 3- or 4-heptyl, 1,1-dimethylhex-1-yl, 2-methylhept-2-yl, 3-methylhept-3-yl, 1,1,2,2-tetramethylprop-1-yl, 1-, 2-, 3- or 4-octyl, 2-ethyloct-1-yl, 1,1,3,3-tetramethylbut-1-yl, 1-methylhept-1-yl, 4-methylhept-1-yl, and also nonyl, decyl, undecyl, dodecyl, tetradecyl, hexadecyl, heptadecyl, octadecyl, nonadecyl, eicosyl and their isomers.

R as alkenyl and alkynyl contains preferably from 2 to 12, especially from 2 to 10, carbon atoms. These radicals correspond especially to the formulae $C_2$–$C_6$alkenyl-$C_nH_{2n}$- and $C_2$–$C_6$alkynyl-$C_nH_{2n}$- in which n is preferably 1, 2 or 3. Examples are vinyl, allyl, crotonyl, but-2- or but-3-en-1-yl, but-1-en-1-yl, but-1-en-3-yl, pent-1-, -2- or -3-en-5-yl, 1,1-dimethylprop-2-en-1-yl, but-2-en-4-yl, hex-1-, -2-, -3- or -4-en-6-yl, hex-2-, -3- or -4-en-6-yl, hex-2-en-4-yl, hex-3-en-5- or -6-yl, hept-1-en-3-, -4-, -5-, -6- or -7-yl, hept-3-en-5- or -6-yl, oct-1-, -2-, -3-, -4-, -5- or -6-en-8-yl, oct-2-en-4-yl, non-7-en-9-yl, dec-8-en-10-yl and corresponding alkyne radicals. Allyl and propargyl are preferred.

R as cycloalkyl contains preferably from 4 to 8, especially 5 or 6, carbon atoms. Examples are cyclopropyl, cyclobutyl, cycloheptyl, cyclooctyl, cyclononyl, cyclodecyl and, especially, cyclopentyl or cyclohexyl.

R as cycloalkylalkyl contains preferably from 4 to 12 carbon atoms and is especially $C_4$–$C_8$cycloalkyl-$C_nH_{2n}$- in which n is 1, 2 or 3. The cycloalkyl is preferably cyclopentyl and cyclohexyl. Examples are cyclopentylmethyl, 1- or 2-cyclopentyleth-1- or -2-yl, cyclohexylmethyl, 1- or 2-cyclohexyleth-1-or -2-yl and 1-, 2- or 3-cyclohexylprop-1- or -2-yl.

R as alkylcycloalkyl contains preferably from 4 to 12 carbon atoms and is especially $C_1$–$C_9$alkyl-$C_4$–$C_8$cycloalkyl. The cycloalkyl is especially cyclopentyl or cyclohexyl. Examples are methyl- or dimethyl-cyclopentyl, ethylcyclopentyl, methyl- or dimethylcyclohexyl, ethyl- or propyl- or butyl-cyclohexyl and methylethylcyclohexyl.

R as alkylcycloalkylalkyl contains preferably from 5 to 12 carbon atoms and is especially $C_1$–$C_4$alkyl-$C_4$–$C_8$-cycloalkyl-$C_nH_{2n}$- in which n is 1, 2 or 3. The cycloalkyl is preferably cyclopentyl or cyclohexyl. Examples are methylcyclohexylmethyl and 1- or 2-(methylcyclohexyl)-eth-1- or -2-yl.

R as aryl contains preferably from 6 to 10 carbon atoms. Examples are phenanthryl, naphthyl and, especially, phenyl.

R as aralkyl contains preferably from 7 to 16, especially from 7 to 12, carbon atoms. The aryl is preferably phenyl. The aralkyl corresponds preferably to the formula phenyl-$C_nH_{2n}$- in which n is 1, 2 or 3. Examples are benzyl, 1- or 2-phenyleth-1- or -2-yl and 1- or 2-phenylprop-1-, -2- or -3-yl.

R as alkaryl contains preferably from 7 to 16 carbon atoms. The aryl is preferably phenyl. R corresponds especially to $C_1$–$C_{10}$alkylphenyl. Examples are methylphenyl, dimethylphenyl, ethylphenyl, methylethylphenyl, n- or iso-propylphenyl, butylphenyl, hexylphenyl, octylphenyl, nonylphenyl and decylphenyl.

As alkaralkyl, R contains preferably from 7 to 16 carbon atoms. The aryl is preferably phenyl. As alkaralkyl, R is especially $C_1$–$C_{16}$alkylphenyl-$C_nH_{2n}$-in which n is 1, 2 or 3. Examples are methylbenzyl, ethylbenzyl, n- or iso-propylbenzyl, butylbenzyl, dimethylbenzyl, octylbenzyl, nonylbenzyl, (methylphenyl)eth-1- or -2-yl and (methylphenyl)prop-1-, -2- or -3-yl.

In a preferred embodiment, R is H or unsubstituted or substituted $C_1$-$C_{12}$alkyl, $C_6$-$C_{10}$aryl, $C_7$-$C_{16}$-aralkyl or alkaryl, or $C_8$-$C_{16}$alkaralkyl, the aryl being especially phenyl. In an especially preferred embodiment, R is H or unsubstituted or substituted $C_1$-$C_8$alkyl, phenyl, phenyl-$C_1$-$C_3$alkyl, $C_1$-$C_4$alkylphenyl or $C_1$-$C_4$alkylphenyl-$C_1$-$C_3$alkyl.

The radical R may be mono- or poly-substituted, preferably mono- to tri-substituted. The substituents may be:

—OH, —CN, halogen, preferably Br, Cl, F;

$C_1$-$C_{12}$-, preferably $C_1$-$C_4$-alkoxy and -alkylthio, for example methoxy, ethoxy, n- or iso-propoxy, butoxy, methylthio, ethylthio;

$C_6$-$C_{10}$aryl-oxy and -thio, especially phenoxy or phenylthio;

$C_7$-$C_{16}$-, preferably $C_7$-$C_{12}$-alkaryl-oxy or -thio; the aryl radical preferably being a phenyl radical, for example methyl-, dimethyl-, ethyl-, methylethyl-, n- or iso-propyl-, butyl-, octyl- and decyl-phenyl-oxy or -thio;

$C_7$-$C_{16}$-, preferably $C_7$-$C_{10}$-aralkyl-oxy and -thio, the aryl radical preferably being a phenyl radical, for example benzyloxy, benzylthio, phenylethoxy;

$C_8$-$C_{16}$-, preferably $C_8$-$C_{12}$-alkaralkyl-oxy and -thio, the aryl radical preferably being a phenyl radical, for example methylbenzyloxy, ethylbenzyloxy, (methylphenyl)ethoxy, methylbenzylthio; —$NR^3R^4$, —$CONR^3R^4$ and —$NR^3COR^6$ in which each of $R^3$ and $R^4$, independently of the other, is preferably $C_1$-$C_4$alkyl, cyclopentyl, cyclohexyl, phenyl or benzyl and $R^6$ is preferably $C_1$-$C_8$acyl. Examples of acyl are formyl, acetyl, propionyl, butanoyl, hexanoyl, benzoyl, chloroacetyl, dichloroacetyl, fluoroacetyl, trichloroacetyl and trifluoroacetyl; —$COOR^5$ and —$OCOR^6$ in which $R^5$ is preferably H or $C_1$-$C_4$alkyl and $R^6$ has the preferred meanings given above.

The substituents alkoxy, alkylthio, aryloxy, arylthio, alkaryl-oxy and -thio, aralkyl-oxy and -thio and alkaralkyl-oxy and -thio may themselves be substituted, for example by —OH, —CN, F, Cl, $C_1$-$C_4$alkoxy, —$NR^3R^4$, —$COOR^5$, —$OCOR^6$, —$CONR^3R^4$ or by —$NR^3COR^6$, $R^3$ to $R^6$ having the meanings and preferred meanings given above. Examples of such substituents are β-chloroethoxy, β-cyanoethoxy, chlorophenoxy, dichlorophenoxy, fluorophenoxy, trifluorophenoxy, chlorotrifluoromethylphenoxy, cyanophenyl, chlorobenzyloxy, (methoxycarbonyl)-ethoxy or -methoxy, acetoxy-ethoxy or -methoxy and dimethylaminocarbonylphenoxy.

$R^1$ as alkyl contains preferably from 1 to 8, especially from 1 to 4, carbon atoms. Preferred examples are methyl, ethyl and n- and iso-propyl. In a preferred embodiment, $R^1$ is H. Preferred substituents of $R^1$ are hydroxy, cyano, F, Cl, carboxy and $C_1$-$C_4$alkoxy.

$R^2$ as alkyl and alkoxy contains preferably from 1 to 6 carbon atoms and is, for example, methyl, ethyl, n- and iso-propyl, n- and iso-butyl, pentyl, hexyl, methoxy, ethoxy, n- and iso-propoxy and n- and iso-butoxy. As aryl, $R^2$ is especially phenyl and, as aryloxy, especially phenoxy. $R^2$ as aralkyl or aralkyloxy is preferably phenyl-$C_nH_{2n}$—(O—)m in which n is 1, 2 or 3 and m is 0 or 1; benzyl and benzyloxy are preferred. $R^2$ as alkaryl or alkaryloxy is preferably $C_1$-$C_4$alkyl-phenyl or -phenoxy, for example methylphenyl, dimethylphenyl and methylphenoxy. $R^2$ as alkaralkyl or alkaralkyloxy is preferably $C_1$-$C_4$alkyl-benzyl or -benzyloxy, for example methylbenzyl or methylbenzyloxy.

In a preferred sub-group, $R^2$ is unsubstituted or substituted $C_1$-$C_6$-alkyl or -alkoxy, phenyl, phenyloxy, benzyl, benzyloxy, $C_1$-$C_4$-alkylphenyl or -alkylphenoxy or $C_1$-$C_4$-alkyl-benzyl or -benzyloxy.

The compounds of formula I that are preferred are those in which R is H, α,α-branched $C_4$-$C_{12}$alkyl, or unsubstituted or methoxy-, nitro- or halo-substituted benzyl, $R^1$ is H or $C_1$-$C_4$alkyl and $R^2$ is H, $C_1$-$C_4$alkyl or $C_1$-$C_4$alkoxy. Of these preferred compounds of formula I the compounds that are, again, especially preferred are those in which R is H or α,α-branched $C_4$-$C_8$alkyl and especially those in which R is H.

The compounds of formula I can be prepared analogously to the process described in EP-A-0 172 140, in which process an azadiene of formula II

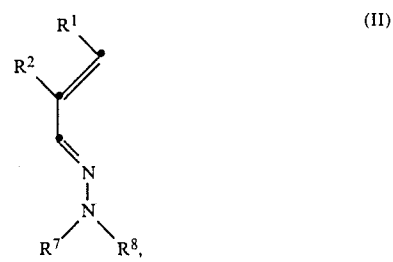

in which each of $R^7$ and $R^8$, independently of the other, has the same meanings as $R^3$ and $R^4$, is reacted with a compound of formula III

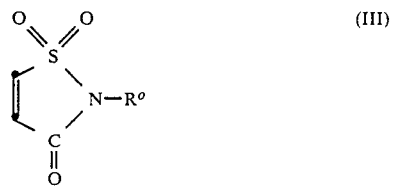

in which R° has the same meaning as R, with the exception of H, to form a compound of formula IV

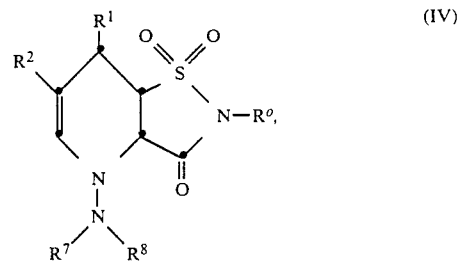

the compound of formula IV is converted into a compound of formula V

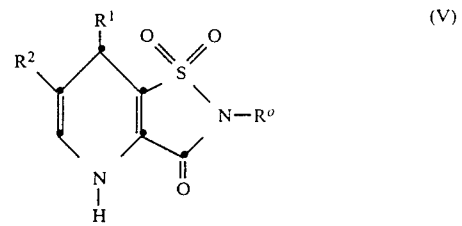

by treatment with an acid and/or by thermal treatment with removal of $R^7R^8NH$, the compound of formula V is oxidised to a compound of formula I, and, for the preparation of compounds of formula I in which R is H, the compound of formula V is reacted with a strong acid.

The process conditions are described in detail in EP-A-0 172 140.

For the removal of the group R° for the preparation of compounds of formula I in which R is H, there are used preferably halogenated aliphatic $C_2$-$C_4$carboxylic acids, for example difluoro- or trifluoroacetic acid, $\alpha,\alpha$-difluoropropionic acid, perfluoropropionic acid or 1,1,1-trifluoro-2,2-dichloropropionic acid.

The unsaturated hydrazones of formula II are known or can be prepared by reacting $\alpha,\beta$-unsaturated aldehydes with N,N-substituted hydrazines. The compounds of formula III are described, for example, in J. of Heteroc. Chem., 8, 571 and 591 (1971) and can be prepared analogously to the processes described therein.

The invention also relates to the compounds of formulae IV and V in which R° has the same meaning as R, with the exception of H. R, $R^1$ and $R^2$ have the preferred meanings given in the case of the compound of formula I.

It has been found that certain compounds of formula I are obtained directly when R° in formula III is an $\alpha,\alpha$-branched aliphatic radical and the reaction is carried out in an organic sulfoxide as solvent.

The invention also relates to a process for the preparation of compounds of formula Ia

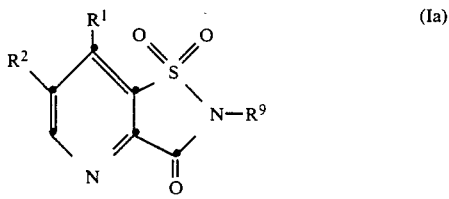

in which $R^1$ and $R^2$ have the meanings given above and $R^9$ is $\alpha,\alpha$-branched $C_4$-$C_{20}$alkyl, $C_5$-$C_{20}$-alkenyl or -alkynyl, 1-($C_1$-$C_4$alkyl)-$C_3$-$C_{10}$cycloalk-1-yl, $\alpha,\alpha$-branched $C_6$-$C_{20}$cycloalkylalkyl, $C_7$-$C_{20}$alkylcycloalkylalkyl, $C_9$-$C_{16}$aralkyl or $C_{10}$-$C_{16}$alkaralkyl, which process comprises reacting a compound of formula II

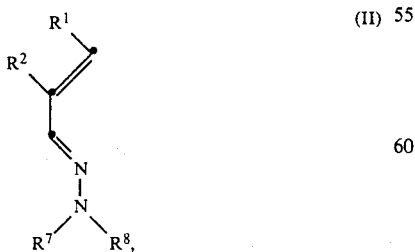

in which each of $R^7$ and $R^8$, independently of the other, has the same meanings as $R^3$ and $R^4$, with a compound of formula IIIa

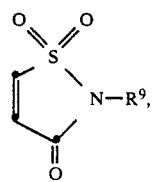

in which $R^9$ has the meaning given above, in the presence of oxygen and an organic sulfoxide as solvent, at elevated temperature and with removal of $R^7R^8NH$.

$R^9$ may be substituted as defined for R in formula I. $R^9$ is especially $\alpha,\alpha$-branched $C_4$-$C_{12}$alkyl. $R^9$ as $\alpha,\alpha$-branched alkenyl or alkynyl contains preferably from 5 to 10 carbon atoms. $R^9$ as 1-($C_1$-$C_4$alkyl)cycloalk-1-yl contains preferably from 4 to 8, especially 5 or 6, carbon atoms in the cycloalkyl radical. $R^9$ as $\alpha,\alpha$-branched cycloalkylalkyl is preferably $C_4$-$C_8$-, especially $C_5$- or $C_6$-cycloalkyl-$C_3$-$C_8$alkyl. $R^9$ as $\alpha,\alpha$-branched alkylcycloalkylalkyl is preferably $C_1$-$C_4$alkyl-$C_4$-$C_8$-, especially -$C_5$- or -$C_6$-cycloalkyl-$C_3$-$C_8$-, especially -$C_3$-$C_6$-alkyl. $R^9$ as $\alpha,\alpha$-branched aralkyl contains especially from 9 to 14 carbon atoms and is especially phenyl-$C_3$-$C_6$alkyl. As alkaralkyl, $R^9$ is preferably $C_1$-$C_4$alkyl-phenyl-$C_3$-$C_6$alkyl. Examples are tert.-butyl, 1,1-dimethyl-but-1-yl or -prop-1-yl, 2-methyl-but-2-yl, 1,1,3,3-tetramethylprop-1-yl, 1,1,2,2-tetra-methylethyl, 1,1-dimethyl-pent-1-yl or -hex-1-yl, 1-methylcyclohex-1-yl, 2-cyclopentylprop-2-yl, 2-(methylcyclohexyl)-prop-2-yl, 2-phenylprop-2-yl and 2-(methylphenyl)-prop-2-yl.

Suitable sulfoxides are, for example, diethyl sulfoxide, methyl ethyl sulfoxide, tetramethylene or pentamethylene sulfoxide and, especially, dimethyl sulfoxide.

The reaction temperature is preferably from 50° to 200° C., especially from 60° to 150° C. The reaction can be carried out in a pure oxygen atmosphere or in oxygen/inert gas mixtures, for example air.

It has also been found that, when using an organic sulfoxide as solvent, compounds of formula I are obtained in a two-stage process, the pyridine ring being formed in the first stage with removal of $R^7R^8NH$.

The invention also relates to a process for the preparation of compounds of formula Ib

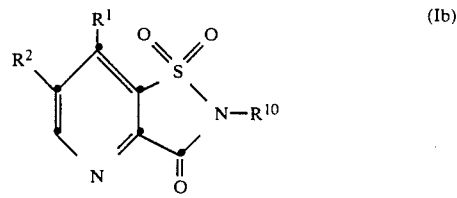

in which $R^1$ and $R^2$ have the meanings given above and $R^{10}$ has the same meaning as R but is not H and does not have the same meaning as $R^9$, which process comprises reacting a compound of formula II (II)

[Chemical structure II: R¹, R² substituted diene with =N-N(R⁷)(R⁸)]

in which each of $R^7$ and $R^8$, independently of the other, has the same meanings as $R^3$ and $R^4$, in the presence of oxygen and an organic sulfoxide as solvent at elevated temperatures, with a compound of formula IIIb (IIIb)

[Chemical structure IIIb: isothiazolinone 1,1-dioxide with N-R¹⁰]

to form a compound of formula VI (VI)

[Chemical structure VI: pyridine with R¹, R², SO₂NHR¹⁰, CON(R⁷)(R⁸)]

and the compound VI is cyclised to a compound of formula Ib with removal of $R^7R^8NH$.

$R^{10}$ has the same preferred meanings as given for R in formula I and the reaction conditions are those preferred for the previously described process.

The cyclisation is preferably carried out with strong acids, for example concentrated sulfuric acid. Glacial acetic acid is advantageously used as solvent.

The isolation of the compounds of formulae I, Ia, Ib, IV, V and VI can be carried out in customary manner, for example by evaporating off the solvent and by filtration, sublimation or distillation. The compounds can be further purified by recrystallisation or by chromatographic methods.

The compounds of formula I are valuable intermediates, for example for the preparation of sulfonylureas that can be used as herbicides (see R. F. Sauers et al., ACS Symposium Series 255, pages 21–28 (1984)).

The following Examples illustrate the invention in more detail. Percentages are percentages by weight unless otherwise indicated. The nomenclature is based on the following structural formula of the 4-azasaccharine:

[Chemical structure: bicyclic azasaccharine skeleton with numbered atoms 1-7]

PREPARATION EXAMPLES

Example 1

18.9 g of 2-ethyl-4-dimethylamino-4-azabutadiene and 12.6 g of 2-tert.-butylisothiazolin-3-one-1,1-dioxide are heated under reflux in 200 ml of ethanol for 8 hours. After concentration by evaporation, the residue is recrystallised from ether/petroleum ether to give 25 g (79% of the theoretical yield) of crystalline compound of formula IVa IVa

[Chemical structure IVa]

Example 2

(a) 6.4 g of 2-methoxyacrolein are stirred for 1 hour at 30°–35° C. with 4.4 g of N,N-dimethylhydrazine in 50 ml of ether, dried at 20° C. with $Na_2SO_4$ and then the solvent is removed. Distillation at 74°–76° C./13 mbar gives 6.2 g of pure 2-methoxy-4-dimethylamino-4-azabutadiene.

(b) 10.8 g of 2-methoxy-4-dimethylamino-4-azabutadiene and 15 g of 2-tert.-butylisothiazolin-3-one-1,1-dioxide are stirred for 1½ h at 80°–85° C. in 250 ml of toluene. The crude bicyclic compound of formula IVb is further processed in the crude state as described in Example 4.

IVb

[Chemical structure IVb]

The compounds listed in Table 1 are obtained in an analogous manner.

TABLE 1

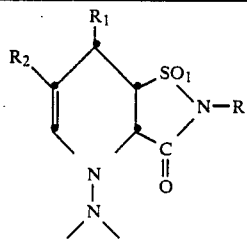

| No. | $R_1$ | $R_2$ | R | m.p. |
|---|---|---|---|---|
| 01.01 | H | $CH_2CH_3$ | tert.-butyl | 90°–92° C. |
| 01.02 | $CH_3$ | $CH_3$ | tert.-butyl | 50°–52° C. |
| 01.03 | H | $CH_3$ | tert.-butyl | |
| 01.04 | H | $CH_2CH_3$ | $-C(CH_3)_2-CH_2C(CH_3)_3$ | |
| 01.05 | H | $OCH_3$ | tert.-butyl | |
| 01.06 | H | $OCH_2$—C$_6$H$_5$ | tert.-butyl | |
| 01.07 | H | $OCH_2CH_3$ | tert.-butyl | |
| 01.08 | $CH_3$ | H | tert.-butyl | |
| 01.09 | $CH_3$ | $OCH_3$ | tert.-butyl | |
| 01.10 | H | $OCH_3$ | $CH_2$—C$_6$H$_5$ | |
| 01.11 | H | $CH_2OCH_3$ | tert.-butyl | |
| 01.12 | H | $SCH_3$ | tert.-butyl | |
| 01.13 | H | $CH(CH_3)_2$ | tert.-butyl | |

Example 3

25 g of cyclo-adduct of the structure according to Example 1 and 55 g of silica gel are heated for 75 minutes at 100° C. in 300 ml of toluene. After removing the silica gel by filtration and rinsing, the yellow solution is concentrated by evaporation and the residue is digested with petroleum ether to give 15.5 g (73%) of yellow powder which is recrystallised from CCl$_4$. Cyclo-adducts substituted in different manners are reacted in an analogous manner. There is obtained

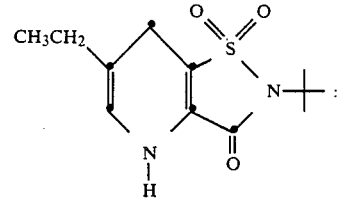

Example 4

9 g of trifluoroacetic acid are added at room temperature to the cyclo-adduct according to Example 2 and the batch is then stirred for 1 hour. The crude bicyclic compound of formula Va is further processed as described in Example 6.

The compounds listed in Table 2 are obtained in an analogous manner.

TABLE 2

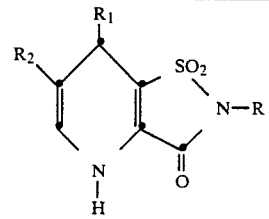

| No. | $R^1$ | $R^2$ | R | m.p. |
|---|---|---|---|---|
| 02.01 | H | $CH_2CH_3$ | tert.-butyl | 161°–163° C. |
| 02.02 | $CH_3$ | $CH_3$ | tert.-butyl | 133°–136° C. |

TABLE 2-continued

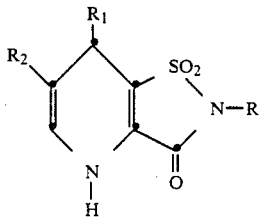

| No. | R¹ | R² | R | m.p. |
|-----|----|----|---|------|
| 02.03 | H | $CH_3$ | tert.-butyl | 178°–179° C. |
| 02.04 | H | $CH_2CH_3$ | $C(CH_3)_2CH_2C(CH_3)_3$ | 109°–113° C. |
| 02.05 | H | $OCH_3$ | tert.-butyl | |
| 02.06 | H | $OCH_2$–C₆H₅ | tert.-butyl | |
| 02.07 | H | $OCH_2CH_3$ | tert.-butyl | |
| 02.08 | $CH_3$ | H | tert.-butyl | |
| 02.09 | $CH_3$ | $OCH_3$ | tert.-butyl | |
| 02.10 | H | $OCH_3$ | $CH_2$–C₆H₅ | |
| 02.11 | H | $CH_2OCH_3$ | tert.-butyl | |
| 02.12 | H | $SCH_3$ | tert.-butyl | |
| 02.13 | H | $CH(CH_3)_2$ | tert.-butyl | |

Example 5

14.1 g of compound having the structure given in Example 3 are heated to 65° C. in 130 ml of glacial acetic acid, and 6.4 g of pyrolusite are added. After one hour at 60° C. the batch is filtered and the filtrate is concentrated by evaporation. The residue is partitioned between water and chloroform. The organic phase is washed twice with water, dried and concentrated by evaporation. The light beige residue is digested with petroleum ether. 13 g (93%) of 6-ethyl-N-tert.-butyl-4-azasaccharine are obtained.

Example 6

Equimolar amounts of 2-methyl-4-dimethylamino-4-azabutadiene and 2-tert.-butylisothiazolin-3-one-2,2-dioxide are heated at from 80° to 90° C. in dimethyl sulfoxide. After one hour the batch is heated to an internal temperature of 100° C. After an induction phase, the reaction becomes exothermic. The heating bath is removed and cooling is effected with a water bath. Stirring is effected for 30 minutes at 100° C. and then the solvent is removed by distillation under a high vacuum and the residue is recrystallised from $CCl_4$ to give a 40% yield of 6-methyl-N-tert.-butyl-4-azasaccharine.

Example 7

12.6 g of bromine are added at room temperature to the cyclo-adduct according to Example 4. 24 g of triethylamine are then added dropwise and the batch is stirred for 15 hours at from 20°–25° C. The suspension is concentrated completely by evaporation, water and ethyl acetate are added and the organic phase is separated off. The latter is concentrated completely by evaporation and the residue is recrystallised from ethanol, thus giving the compound of formula Ic which has a melting point of 216°–217° C.

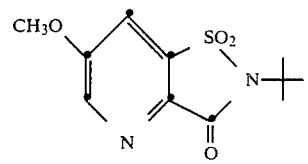

Ic

TABLE 3

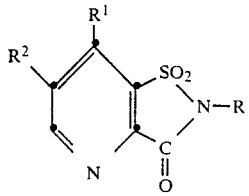

| No. | R¹ | R² | R | m.p. |
|-----|----|----|---|------|
| 03.01 | H | $CH_2CH_3$ | tert.-butyl | 149°–151° C. |
| 03.02 | $CH_3$ | $CH_3$ | tert.-butyl | 150°–152° C. |

TABLE 3-continued

[Structure: pyridine ring with R¹, R² substituents, fused to isothiazolinone with SO₂-N-R and C=O]

| No. | R¹ | R² | R | m.p. |
|---|---|---|---|---|
| 03.03 | H | CH₃ | tert.-butyl | 170°-172° C. |
| 03.04 | H | CH₃ | C(CH₃)₂CH₂C(CH₃)₃ | 221°-222° C. |
| 03.05 | H | OCH₃ | tert.-butyl | 216°-217° C. |
| 03.06 | H | OCH₂—C₆H₅ | tert.-butyl | |
| 03.07 | H | OCH₂CH₃ | tert.-butyl | |
| 03.08 | CH₃ | H | tert.-butyl | |
| 03.09 | CH₃ | OCH₃ | tert.-butyl | |
| 03.10 | H | OCH₃ | CH₂—C₆H₅ | |
| 03.11 | H | CH₂OCH₃ | tert.-butyl | |
| 03.12 | H | SCH₃ | tert.-butyl | |
| 03.13 | H | CH(CH₃)₂ | tert.-butyl | 123°-125° C. |

Example 8

11.5 g of compound according to Example 7 are heated at 120° C. in 42 ml of trifluoroacetic acid. After 3 hours, the batch is concentrated by evaporation and the residue is digested with ethyl acetate/diethyl ether. The powder is isolated by filtration and dried in vacuo to give 6-ethylazasaccharine in a yield of 60% and with a melting point of 199°-201° C.

TABLE 4

[Structure: pyridine ring with R¹, R² substituents, fused to isothiazolinone with SO₂-NH and C=O]

| No. | R¹ | R² | m.p. |
|---|---|---|---|
| 04.01 | H | CH₂CH₃ | 199°-201° C. |
| 04.02 | CH₃ | CH₃ | 267°-270° C. |
| 04.03 | H | CH₃ | 215°-217° C. |
| 04.04 | H | OCH₃ | 255°-256° C. |
| 04.05 | H | OCH₂—C₆H₅ | |
| 04.06 | H | OCH₂CH₃ | |
| 04.07 | CH₃ | H | |
| 04.08 | CH₃ | OCH₃ | |
| 04.09 | H | CH₂OCH₃ | |
| 04.10 | H | CH(CH₃)₂ | 199°-202° C. |

Example 9

The procedure is the same as in Example 6 and 2-methyl-4-dimethylamino-4-azabutadiene is reacted with an isothiazoline which has been substituted at the N atom by benzyl or p-methoxybenzyl. There is obtained

[Structure: pyridine ring with R¹, R², SO₂NHR, CH₃, and CON(CH₃)₂ substituents]

| Example no. | R¹ | R² | R | melting point (°C.) | yield (%) |
|---|---|---|---|---|---|
| 10 | H | CH₃ | benzyl | 169-170 | 43 |
| 11 | H | CH₃ | p-methoxybenzyl | 141-143 | 42 |

Example 12

5.0 g of compound according to Example 10 are heated for 20 hours at 100° C. in 30 ml of glacial acetic acid and 0.75 g of concentrated sulfuric acid. The reaction mixture is concentrated by evaporation, the residue is dissolved in chloroform and washed with 1N NaHCO₃ solution. The organic phase is dried over MgSO₄ and then concentrated by evaporation. Digestion is then effected with diethyl ether to give 3.9 g (90%) of 6-methyl-N-benzyl-4-azasaccharine in the form of beige crystals having a melting point of 167°-170° C.

Application Example

(a) Preparation of a sulfonylurea 1 mol of 6-methyl-4-azasaccharine is suspended in 10 times the volume of methanol and heated at 100° C. with 1/10 molar equivalent of concentrated sulfuric acid in a bomb tube. After 18 hours the batch is concentrated by evaporation and the residue is washed with CHCl₃/NaHCO₃ to give 3-(aminosulfonyl)-5-methyl-pyridine-2-carboxylic acid methyl ester in the form of a beige powder having a melting point of 86°-88° C.

1 mol of the ester is dissolved in acetonitrile, and a solution of 5-methyl-3-methoxy-1-(phenoxycarbonylamino)triazine in acetonitrile is added dropwise thereto over a period of 75 minutes. After stirring for one hour, the batch is concentrated by evaporation, the residue is taken up in water, and 1 molar equivalent of 1N HCl is added dropwise. The precipitate is isolated by filtration and dried to give

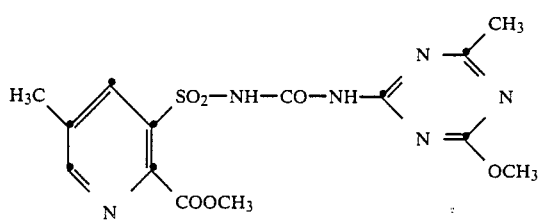

which has a melting point of 168°-170° C.

(b) Demonstration of herbicidal action in pre-emergence application

In a greenhouse, plant seeds of dicotyledonous and monocotyledonous weeds are sown in pots 11 cm in diameter. Immediately afterwards, the surface of the soil is treated with an aqueous dispersion or solution of the test compounds. Concentrations of 0.5, 0.125 and 0.03 kg of test compound per hectare are used. The pots are then kept in the greenhouse at a temperature of 22°-25° C. and 50-70% relative humidity. After 3 weeks the test is evaluated and the action is assessed in accordance with the following scale of ratings:

1 plant has not germinated or has withered.
2-3 very pronounced action.
4-6 medium action.
7-8 weak action.
9 no action (as untreated control).

| | Test results (pre-emergent) | | |
|---|---|---|---|
| | action application rate kg/ha | | |
| Test plant | 0,500 | 0,125 | 0,03 |
| Alopecurus myos. | 3 | 4 | 5 |
| Echinochloa c.g. | 2 | 3 | 7 |
| Amaranthus ret. | 2 | 2 | 3 |
| Chenopodium Sp. | 3 | 4 | 7 |
| Sinapsis | 2 | 2 | 2 |
| Stellaria | 3 | 4 | 4 |
| Chrysanth. leuc. | 2 | 2 | 3 |
| Galium aparine | 2 | 3 | 5 |
| Viola tricolor | 2 | 2 | 2 |
| Veronica Sp. | 2 | 3 | 3 |

What is claimed is:

1. A process for the preparation of a compound of formula I

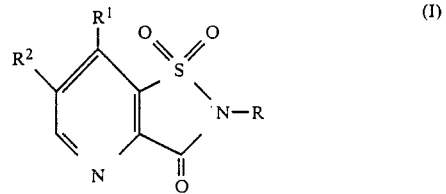

in which

R is H, linear or branched $C_1$-$C_{20}$alkyl, $C_2$-$C_{20}$alkenyl or $C_2$-$C_{20}$alkynyl, $C_3$-$C_{10}$cycloalkyl, $C_4$-$C_{20}$cycloalkylalkyl, $C_4$-$C_{20}$alkylcycloalkyl, $C_5$-$C_{20}$alkylcycloalkylalkyl, $C_6$-$C_{14}$aryl, $C_7$-$C_{20}$aralkyl or -alkaryl or $C_8$-$C_{20}$alkaralkyl, each of which is unsubstituted or substituted by —OH, —CN, halogen, $C_1$-$C_{12}$-alkoxy or -alkylthio, $C_6$-$C_{10}$aryl-oxy or -thio, $C_7$-$C_{16}$-aralkyloxy, -alkaryloxy, -aralkylthio or -alkarylthio, $C_8$-$C_{18}$alkaralkyloxy or -thio, —NR³R⁴, —COOR⁵, —OCOR⁶, —CONR³R⁴ or by —NR³COR⁶, in which each of R³ and R⁴, independently of the other, is $C_1$-$C_{12}$alkyl, $C_5$- or $C_6$-cycloalkyl, $C_6$-$C_{10}$aryl, $C_7$-$C_{16}$aralkyl or $C_8$-$C_{16}$alkaralkyl or R³ and R⁴ together are tetra- or penta-methylene or 3-oxapentylene, R⁵ is H, $C_1$-$C_{12}$alkyl, phenyl, benzyl, cyclohexyl or cyclopentyl and R⁶ is $C_1$-$C_{12}$acyl, R¹ is H, or linear or branched $C_1$-$C_{12}$alkyl which is unsubstituted or substituted by hydroxy, halogen, cyano, $C_1$-$C_4$alkoxy, carboxy, $C_1$-$C_{12}$acyloxy or by $C_1$-$C_4$alkoxycarbonyl, R² is H, or $C_1$-$C_{12}$-alkyl or -alkoxy, $C_6$-$C_{10}$-aryl or -aryloxy, $C_7$-$C_{16}$-aralkyl, -alkaryl, -alkaryloxy or -aralkyloxy, or $C_8$-$C_{16}$alkaralkyloxy, which are unsubstituted or substituted by hydroxy, halogen, cyano, $C_1$-$C_4$alkoxy, carboxy, $C_1$-$C_{12}$acyloxy or by $C_1$-$C_4$alkoxycarbonyl, in which an azadiene of formula II

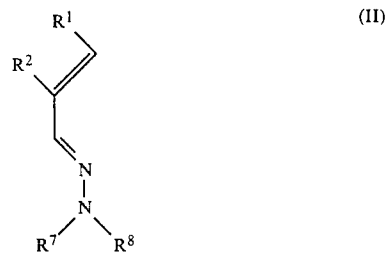

in which each of R⁷ and R⁸, independently of the other, has the same meanings as R³ and R⁴, is reacted with a compound of formula III

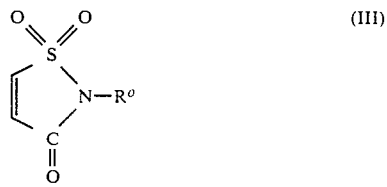

in which R° has the same meaning as R, with the exception of H, to form a compound of formula IV the compound of formula IV is converted into a compound of formula V

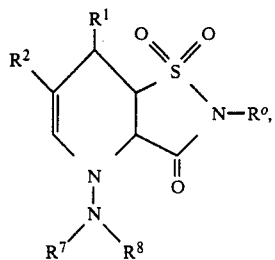
(IV)

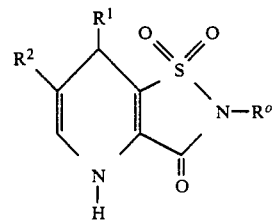
(V)

by treatment with an acid and/or by thermal treatment with removal of $R^7R^8NH$, the compound of formula V is oxidized to a compound of formula I, and, for the preparation of compounds of formula I in which R is H, the compound of formula V is reacted with a strong acid.

2. A process according to claim 1, which is carried out at a temperature of from 50° to 200°.

* * * * *